(12) United States Patent
Lawandy

(10) Patent No.: US 6,441,380 B1
(45) Date of Patent: Aug. 27, 2002

(54) CODING AND AUTHENTICATION BY PHASE MEASUREMENT MODULATION RESPONSE AND SPECTRAL EMISSION

(75) Inventor: Nabil M. Lawandy, North Kingstown, RI (US)

(73) Assignee: Spectra Systems Corporation, Providence, RI (US)

(*) Notice: Subject to any disclaimer, the term of this patent is extended or adjusted under 35 U.S.C. 154(b) by 35 days.

(21) Appl. No.: 09/686,154

(22) Filed: Oct. 11, 2000

Related U.S. Application Data

(60) Provisional application No. 60/159,171, filed on Oct. 13, 1999.

(51) Int. Cl.[7] .................................................. G06K 7/10
(52) U.S. Cl. .................................. 250/458.1; 250/459.1
(58) Field of Search .......................... 250/458.1, 459.1, 250/271, 461.1

(56) References Cited

U.S. PATENT DOCUMENTS

| | | | |
|---|---|---|---|
| 3,513,320 A | 5/1970 | Weldon | 250/219 |
| 3,902,047 A | 8/1975 | Tyler et al. | 235/61.11 E |
| 4,044,227 A | 8/1977 | Holm et al. | 235/61.7 R |
| 4,924,088 A | 5/1990 | Carman et al. | 250/271 |
| 4,937,457 A * | 6/1990 | Mitchell et al. | 250/458.1 |
| 5,128,528 A | 7/1992 | Byrne | 235/470 |
| 5,294,799 A | 3/1994 | Aslund et al. | 250/458.1 |
| 5,418,855 A | 5/1995 | Liang et al. | 380/23 |
| 5,448,582 A | 9/1995 | Lawandy | 372/42 |
| 5,459,323 A * | 10/1995 | Morgan | 250/458.1 |
| 5,485,530 A | 1/1996 | Lakowicz et al. | 382/191 |
| 5,608,225 A | 3/1997 | Kamimura et al. | 250/458.1 |
| 5,667,300 A * | 9/1997 | Mandelis et al. | 374/43 |
| 5,881,886 A | 3/1999 | Lawandy | 209/3.3 |
| 5,920,056 A | 7/1999 | Bonnet | 235/383 |
| 5,955,737 A | 9/1999 | Hallidy et al. | 250/458.1 |
| 6,285,894 B1 * | 9/2001 | Oppelt et al. | 600/322 |

FOREIGN PATENT DOCUMENTS

| | | |
|---|---|---|
| DE | 0 578859 A1 | 7/1992 |
| EP | 0 509 280 A2 | 10/1992 |
| EP | 0 578 859 A1 | 1/1999 |
| GB | 2 095 822 A | 10/1982 |

OTHER PUBLICATIONS

"Sequential–Readout Identification tag" by Dickerson, et al., IBM Technical Disclosure Bulletin, vol. 17 No. 3 Aug. 1974, pps. 782–783.

"Generation of stimulated noncoherent radiation in light–scattering media exhibiting chemical reactions" by Izmallov, et al., Institute of Semiconductors, Academy of Sciences of the Ukranian SSR, Kiev, Apr. 12, 1981, pps. 588–594.

"Generation of Light by a Scattering Medium with Negative Resonance Absorption" by Letokhov, P.N. Lebedev Physics Institute, USSR Academy of Sciences, 1967, pps. 835–840.

* cited by examiner

Primary Examiner—Constantine Hannaher
Assistant Examiner—Otilia Gabor
(74) Attorney, Agent, or Firm—Harrington & Smith, LLP

(57) ABSTRACT

A method of coding and authentication includes the steps of irradiating a sample with a harmonically modulated radiation and detecting a component of an emission of the sample in response where the component is out of phase with the radiation. The method further includes modulating the intensity of the radiation and identifying the sample by a phase difference between the radiation and the out of phase component.

23 Claims, 2 Drawing Sheets

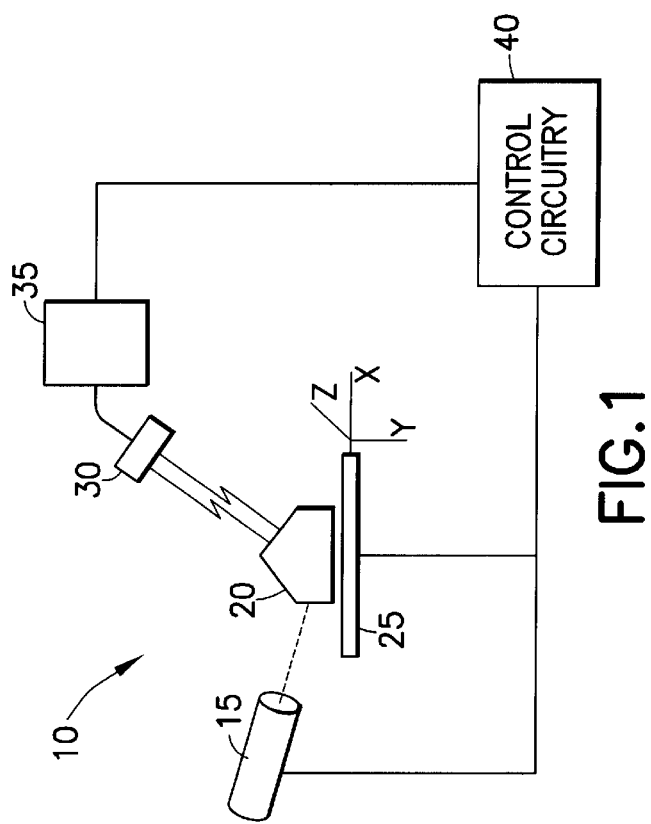
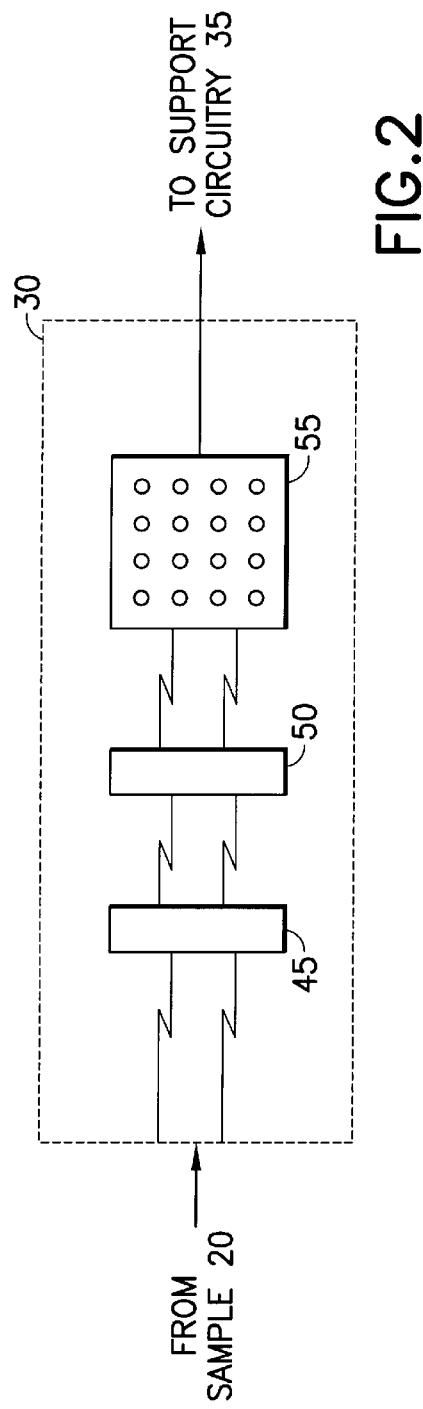

CODING AND AUTHENTICATION BY PHASE MEASUREMENT MODULATION RESPONSE AND SPECTRAL EMISSION

This application claims benefit of provisional application Ser. No. 60/159,171 filed Oct. 13, 1999.

FIELD OF THE INVENTION

This invention relates to coding and authentication, in particular, by identifying spectral emissions and a response to modulated excitation.

BACKGROUND OF THE INVENTION

It is well known that valuable items, for example, negotiable instruments, works of art, etc. are susceptible to theft and counterfeiting.

With regard to documents, the advancement of color copier technology has made it fairly easy to create a color copy of any document, including currency, using commonly available equipment.

One way of protecting valuable items is to utilize the physical characteristics of the item itself as a way to identify the object. As an example, watermarks or signatures are typically produced by taking semantic information of the item to be protected, for example, alphanumeric characters, physical features, etc. or other related information (e.g. ownership information), as an input to a mathematical algorithm that generates a signature or watermark. These signatures or watermarks are typically kept with the item to be authenticated. For example, a digital watermark may be imbedded within digital information to be protected or it may be printed on or within an item that is valuable. In another example, the watermark or signature may be kept separate from the item, but when combined with the item to be authenticated produces proof of authentication. For instance, a smart card could be utilized that when read confirms certain physical characteristics about an item.
Objects and Advantages of the Invention It is a first object and advantage of this invention to provide a system for coding and authenticating an item.

It is another object and advantage of this invention to code and authenticate an item by using a response to a specific periodic optical excitation.

SUMMARY OF THE INVENTION

The foregoing and other problems are overcome and the objects of the invention are realized by methods and apparatus in accordance with embodiments of this invention.

A method of coding and authentication includes the steps of irradiating a sample with a harmonically modulated radiation and detecting a component of an emission of the sample in response, where the component is out of phase with the radiation. The method further includes modulating the intensity of the radiation and identifying the sample by a phase difference between the radiation and the out of phase component.

BRIEF DESCRIPTION OF THE DRAWINGS

The above set forth and other features of the invention are made more apparent in the ensuing Detailed Description of the Invention when read in conjunction with the attached Drawings, wherein:

FIG. 1 depicts a detection system 10 in accordance with the invention;

FIG. 2 shows a block diagram of a detector array;

DETAILED DESCRIPTION OF THE INVENTION

Figure 3:
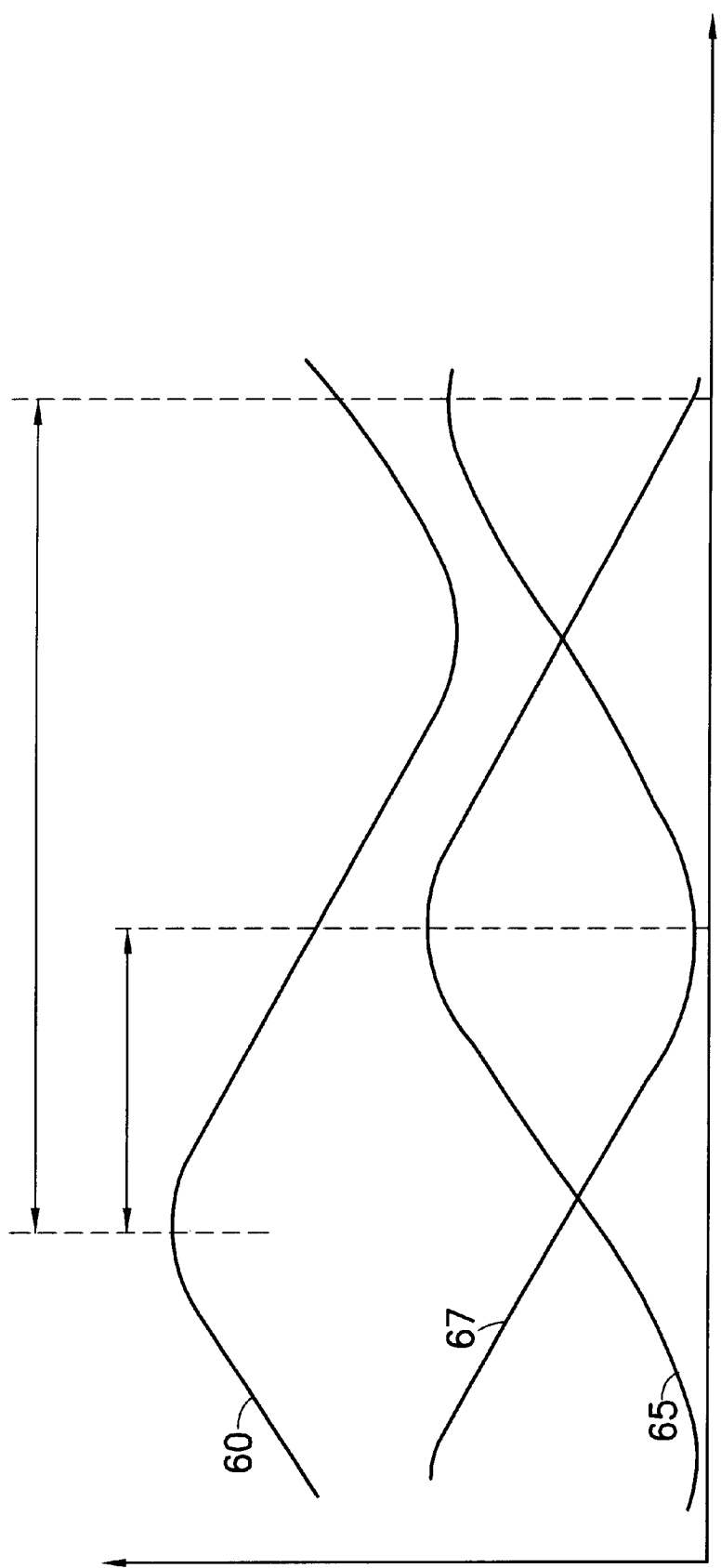
FIG. 3 shows a representation of the phase angle difference between the output of a source and the emissions from a sample.

The invention is directed toward a method and apparatus for authenticating an article or document by its steady state temporal response. Specifically, a shift in phase of an oscillating fluorescence or phosphorescence time signal is manifested when an object is subjected to a periodic excitation. An atomic or molecular fluorescent material system with two or more levels may be optically excited to exhibit a steady state time signature in response to the periodic optical excitation. Through solution of the appropriate rate equations, a particular radiating transition will fluoresce or radiate light with a time signature that is a function of the modulated excitation and the specific delay rates of the system.

The same effect can be used with any physical response that has associated with it a well defined relaxation process and/or time including non-linear phenomena.

An atomic or molecular fluorescent material system with two or more levels typically exhibits an upper state lifetime $T$ or relaxation rate of $\gamma = T^{-1}$. This response phenomena can be driven by a harmonic forcing function (exciting UV light for example) whose intensity is harmonically modulated. It should be understood that, as employed herein, harmonic modulation means modulating in relationship to the relaxation rates of the materials being driven to an upper state. The forcing function is modulated in a manner that does not preclude detecting emissions from a sample that have characteristics that result from the modulation. The forcing function is given by:

$$1 = I_0 \cos \omega t \quad (1)$$

With this modulation, the electron population of the upper emitting state is given by:

$$N_u = N_0 B I_0 \cos \omega t - N_{u\gamma} \quad (2)$$

where it is assumed that there is, on a time scale $T$, $\omega^{-1}$, a direct excitation from the ground state $N_0$, and that $B$ is the effective Einstein coefficient for the transition, and $I_0$ is the excitation intensity.

Assuming a solution of the form:

$$N_U(t) = N_U^A \cos \omega t + N_U^B \sin \omega t \quad (3)$$

we obtain:

$$N_U(t) = -\omega N_U^A \sin \omega t + \omega N_U^B \cos \omega t \quad (4)$$

Insertion of equations (3) and (4) in equation (2) yields:

$$-\omega N_U \sin \omega t = -N_U^B \gamma \sin \omega t \quad (5a)$$

and $$+\omega N_U^B \cos \omega t = N_0 B I \cos \omega t - N_U^A \cos \omega t \quad (5b)$$

These two equations can be solved to yield:

$$N_u^A = N_U^B \frac{\gamma}{\omega} \text{ and} \quad (6a)$$

$$N_u^B = \left(\frac{\omega}{\omega^2 + \gamma^2}\right) N_O BI \qquad (6b)$$

Equation 6a can be used to determine the phase angle of the emitted light, φ, at a modulation frequency, ω:

$$\phi = \mathrm{Tan}^{-1}\left(\frac{\omega}{\gamma}\right). \qquad (7)$$

Equation 7 shows that when $\omega=\gamma$, $\phi=\pi/4$ or 45 degrees.

The out of phase or quadrature component of the fluorescent emission of a material "i" at a wavelength λ is given by:

$$I_i^\lambda = I_o A\left(\frac{\omega}{\omega^2 + \gamma_i^2}\right) \qquad (8)$$

where $I_0$ is the excitation peak amplitude, A is a factor that depends on the material active density, other rates and optical cross section. $\gamma_i$ is the relaxation rate of the optically emitting level and includes non radiative relaxation.

In the case that a combination of different materials are used, all emitting at or near the same wavelength λ but with different $\gamma_i$, the quadrature component of the fluorescent light output has an amplitude given by:

$$\sum_{i=1}^{N} I_i^\lambda \qquad (9)$$

This enables the encoding of information into substantially one "color", by discriminating the plurality of relaxation values by the associated phase shifts.

Equation (8) shows a resonance response behavior which peaks at $\omega=\gamma_i$ and has a full width at half maximum given by:

$$\Delta\omega_i = 2\sqrt{3}\gamma_i \qquad (10)$$

Equation (10) shows that materials with the same λ can all be distinguished from each other by their component or out of phase response if their $\gamma_i$ are well separated. The critical separation is of the order of:

$$\frac{\gamma_{i+1}}{\gamma_i} > \frac{2+\sqrt{3}}{2-\sqrt{3}} > 14 \qquad (11)$$

Using $\gamma_{i+1}/\gamma_i > 20$, we find that between a range of 10 Hz and 10 MHz, we can uniquely identify four materials with the same emission wavelength using their time response.

The temporal response of a material system may be combined with spectral response to obtain a number of unique response signatures. Excitation in the UVA region alone or with other sources can be used to produce fluorescent or phosphorescent emission out to 1000 nm or more. Using the range from 400 nm to 1000 nm (silicon response window) and a typical spectral separation requirement for dyes of 100 nm we can obtain different fluorescent wavelength bins $\lambda_1 \ldots \lambda_M$, where M is approximately 5.

By sweeping the modulation frequency of the excitation source from 1 Hz to 10 MHz and phase detecting the fluorescent light within each wavelength bin, we can obtain up to $M^N$ unique codes. For the case of M=5, and N=4, we have $\gamma_N^M=625$ available codes.

Phase measurement of frequencies well into the MHz range can be effectively implemented using currently available lock in circuits on a single chip. Such chips can determine phase differences with approximately 1% accuracy, which allows for a high precision authentication of the specific fluorescent taggant material based on time response as well as spectral signature.

A detection system 10 in accordance with the invention is shown in FIG. 1. A modulated source of radiation 15 excites a sample 20 at a wavelength ω and a periodic rate defined by Equation 8. The source 15 preferably generates UV radiation but may generate any type of radiation that is capable of being harmonically modulated. The sample may be mounted on a positioning device 25 in order to locate the sample 20 for irradiation. The source 15 and detector array 30 may also comprise positioning devices (not shown) for locating these devices for optimum performance. In response to being irradiated by the source 15, the sample 20 emits a wavelength λ with a time function defined by the modulated wavelength ω and the specific relaxation rate γ of the sample 20. A detector array 30 with appropriate support circuitry 35 detects the emission from the sample 20. The detector array is preferably capable of detecting the spectral content of the emission in addition to any phase differences of emissions having the same wavelength. Control circuitry 40 directs the activity of the overall system 10 and in particular controls the source 15, positioning device 25, detector array 30 and support circuitry 35.

As shown in FIG. 2, the detector array 30 is preferably comprised of an optical section 45 for focusing the emissions within the detector array 30, an array of sensors 55 for detecting the emissions, and a filter section 50 for allowing only the frequencies of interest to impinge on the sensors 55. The sensor array may comprise any array of sensors suitable for detecting the emissions of the sample 55, for example, a diode array, a CCD array, etc.

As a specific example, the sensors 55 may comprise three photodiodes and the filter section 50 may comprise a corresponding number of narrow band filters, one diode filter combination centered on the emission line, and the two others being, for example, +−10 nm relative to the center of the emission line. The relative signal outputs of each diode filter combination serve to authenticate the spectral signature while phase shift measurements authenticate the temporal signature of the specific material.

FIG. 3 shows a representation of the phase angle difference between the output 60 of the source 15 and the emissions 65, 67 from the sample 20.

It can be appreciated that the techniques and structures described above are useful for authenticating objects based on their materials. It can also be appreciated that by selecting certain materials with the characteristics described above when constructing items, that the techniques and structures disclosed herein are also useful for encoding various types of information into objects, and authenticating those objects, such as valuables, negotiable instruments, works of art, currency, various types of substrates, items that may require sorting, items that are traveling on a conveyor system, etc.

Thus, while the invention has been particularly shown and described with respect to preferred embodiments thereof, it will be understood by those skilled in the art that changes in form and details may be made therein without departing from the scope and spirit of the invention.

What is claimed is:

1. A method of coding and authentication comprising the steps of:

irradiating a sample with a harmonically modulated radiation, the sample comprising at least one material that exhibits a relaxation rate to a first energy level when excited to a second energy level, where the radiation is harmonically modulated in relationship to the relaxation rate; and detecting a component of an emission of said sample in response to said irradiating wherein said component is out of phase with said radiation, and where the detected component is expressive of encoded information.

2. The method of claim 1 wherein said harmonically modulated radiation is modulated with respect to intensity.

3. The method of claim 2 further comprising identifying said sample by a phase difference between said radiation and said out of phase component.

4. The method of claim 2 wherein said sample is comprised of material having a particular emission relaxation rate which determines the phase difference between said out of phase component and said radiation.

5. The method of claim 2 wherein said step of detecting comprises detecting a plurality of out of phase components, each relating to a relaxation rate γ, of a particular material wherein each of said relaxation rates have relative values defined by the equation:

$$\frac{\gamma_{i+1}}{\gamma_i} > \frac{2+\sqrt{3}}{2-\sqrt{3}} > 14.$$

6. The method of claim 1 wherein said harmonically modulated radiation is modulated with respect to frequency.

7. The method of claim 6 wherein said step of detecting comprises detecting a plurality of emission wavelengths, each emission wavelength comprising at least one component that is out of phase with said radiation.

8. An apparatus for detecting spectral emission comprising:

a source for irradiating a sample with a harmonically modulated radiation, the sample comprising at least one material that exhibits a relaxation rate to a first energy level when excited to a second energy level, where the radiation is harmonically modulated in relationship to the relaxation rate; and a detector for detecting a component of an emission of said sample in response to said irradiating wherein said component is out of phase with said radiation, and where the detected component is expressive of encoded information.

9. The apparatus of claim 8 wherein said harmonically modulated radiation is modulated with respect to intensity.

10. The apparatus of claim 9 further comprising circuitry coupled to said detector for wherein said circuitry determines the amount of phase difference between said radiation and said out of phase component and identifies said sample according to said amount of phase difference.

11. The apparatus of claim 8 wherein said harmonically modulated radiation is modulated with respect to frequency.

12. The apparatus of claim 11 further comprising circuitry coupled to said detector wherein said circuitry identifies a plurality of emission wavelengths, each emission wavelength comprising at least one component that is out of phase with said radiation.

13. A method of coding and authentication comprising the steps of:

irradiating a sample with a harmonically modulated radiation, the sample comprising materials that exhibit characteristic relaxation rates to a first energy level when excited to a second energy level, where the radiation is harmonically modulated in relationship to the relaxation rates; and detecting a plurality of components of an emission of said sample, wherein said plurality of components are related to said relaxation rates of said materials that comprise said sample and encode information.

14. A method as in claim 13, and further comprising decoding the information based on said plurality of detected components.

15. A method for encoding information, comprising:

providing an object with a plurality of light emissive materials selected for encoding information based on a characteristic relaxation rate of each of the plurality of materials, the relaxation rate being to a first energy level when excited to a second energy level;

illuminating the plurality of materials with light that is harmonically modulated in relationship to the relaxation rates;

detecting emitted light from the plurality materials and determining phase differences in the emitted light relative to the harmonically modulated light; and decoding the encoded information using the determined phase differences.

16. A method as in claim 15, where the step of illuminating comprises varying a modulation frequency of the harmonically modulated light over a range of frequencies, and where the steps of detecting and decoding occur for a plurality of different modulation frequencies.

17. Apparatus for reading encoding information, comprising:

an optical source for illuminating an object with harmonically modulated light, the object being provided with a plurality of light emissive materials selected for encoding information based on a characteristic relaxation rate of the materials, the relaxation rate being to a first energy level when excited to a second energy level, the light being harmonically modulated in relationship to the relaxation rates;

a detector for detecting emitted light from the material and for determining phase differences between the emitted light and the harmonically modulated light; and a decoder coupled to said detector for decoding the encoded information using the determined phase differences.

18. Apparatus as in claim 17, where said source varies a modulation frequency of the harmonically modulated light over a range of frequencies, and where said detector and said decoder are responsive to a plurality of different modulation frequencies.

19. Apparatus as in claim 17, where the information comprises information that identifies the object.

20. Apparatus as in claim 17, where the information comprises information that authenticates the object.

21. Apparatus as in claim 17, where the object comprises currency, and where the information comprises information that authenticates the currency.

22. Apparatus as in claim 17, where said apparatus is coupled to means for sorting objects having the encoded information.

23. Apparatus as in claim 17, where said detector and decoder are further responsive to emitted wavelengths of the materials, where the emitted wavelengths encode information about the object.

* * * * *